United States Patent
Wallace

(10) Patent No.: US 12,415,094 B2
(45) Date of Patent: Sep. 16, 2025

(54) SYSTEM AND METHOD FOR FACILITATING SHEDDING OF TISSUE LINING CELLS WITH ULTRASOUND

(71) Applicant: GE Precision Healthcare LLC, Wauwatosa, WI (US)

(72) Inventor: Kirk D. Wallace, Glenville, NY (US)

(73) Assignee: GE PRECISION HEALTHCARE LLC, Wauwatosa, WI (US)

( * ) Notice: Subject to any disclaimer, the term of this patent is extended or adjusted under 35 U.S.C. 154(b) by 175 days.

(21) Appl. No.: 18/192,945

(22) Filed: Mar. 30, 2023

(65) Prior Publication Data
US 2024/0325792 A1 Oct. 3, 2024

(51) Int. Cl.
*A61N 7/00* (2006.01)
*A61B 10/00* (2006.01)

(52) U.S. Cl.
CPC ............ *A61N 7/00* (2013.01); *A61B 10/0045* (2013.01); *A61N 2007/0039* (2013.01); *A61N 2007/0052* (2013.01); *A61N 2007/0056* (2013.01)

(58) Field of Classification Search
CPC .............. A61N 7/00; A61N 2007/0039; A61N 2007/0052; A61N 2007/0056; A61B 10/0045
See application file for complete search history.

(56) References Cited

U.S. PATENT DOCUMENTS

| 2010/0191110 A1* | 7/2010 | Insana ................. G01S 7/52022 600/438 |
| 2013/0096430 A1* | 4/2013 | Yoshiara ............ A61B 17/3403 600/443 |

(Continued)

FOREIGN PATENT DOCUMENTS

WO    2019183623 A1    9/2019

OTHER PUBLICATIONS

Blackstone et al., Intraductal aspiration for cytodiagnosis in pancreatic malignancy, Gastrointestinal Endoscopy, Feb. 1977, sheets 4, vol. 23, Issue 3, Abstract.

(Continued)

*Primary Examiner* — Dixomara Vargas
(74) *Attorney, Agent, or Firm* — Daugherty & Del Zoppo, Co. LPA

(57) ABSTRACT

An ultrasound system includes transmit circuitry configured to produce a push pulse electrical excitation signal and a transducer array configured to receive the push pulse electrical excitation signal and transmit a push pulse that produces acoustic and shear wave propagation in tissue of interest, where the push pulse is based on a pre-determined set of parameters stored in computer readable medium. A computer-implemented method includes producing a push pulse electrical excitation signal and includes transmitting, based on the push pulse electrical excitation signal, a push pulse that produces acoustic and shear wave propagation in tissue of interest. A computer readable medium is encoded with computer executable instructions, which, when executed by a processor, cause the processor to perform the method. In one instance, the push pulse promotes shedding of lining cells of the tissue of interest in connection with a biopsy of shed cells for the tissue of interest.

20 Claims, 9 Drawing Sheets

(56) References Cited

U.S. PATENT DOCUMENTS

| | | | |
|---|---|---|---|
| 2017/0231602 A1* | 8/2017 | Venkataraman | A61B 8/085 |
| | | | 600/431 |
| 2018/0140279 A1* | 5/2018 | Perrey | A61B 8/5223 |
| 2019/0142366 A1* | 5/2019 | Meral | A61B 8/485 |
| | | | 600/438 |
| 2021/0106312 A1* | 4/2021 | Meral | A61B 8/461 |
| 2021/0113192 A1* | 4/2021 | Meral | G16H 50/50 |
| 2021/0275835 A1 | 9/2021 | Adam | |
| 2022/0142614 A1* | 5/2022 | Labyed | G16H 50/20 |
| 2022/0313217 A1* | 10/2022 | Freeman | G01S 7/52022 |
| 2024/0090823 A1* | 3/2024 | Sadeghi | A61B 8/465 |
| 2024/0156441 A1* | 5/2024 | Labyed | A61B 8/463 |

OTHER PUBLICATIONS

Endo, et al., Cytodiagnosis of pancreatic malignant tumors by aspiration, under direct vision, using a duodenal Fiberscope, Gastroenterology, 1975, pp. 944-951, vol. 67, No. 5.

Nakaizumi, et al., Cytologic Examination of Pure Pancreatic Juice in the Diagnosis of Pancreatic Carcinoma, The Endoscopic Retrograde Intraductal Catheter Aspiration Cytologic Technique, Cancer, 1992, vol. 70, p. 2610-2614.

\* cited by examiner

SYSTEM AND METHOD FOR FACILITATING SHEDDING OF TISSUE LINING CELLS WITH ULTRASOUND

FIELD

The following generally relates to ultrasound, and more particularly for facilitating shedding of tissue lining cells with ultrasound.

BACKGROUND

Ductal lining cells are commonly found in organs (e.g. the pancreas, the prostate, the breast, the salivary gland, etc.). These cells have rapid turn-over rates and are continuously shed through normal physiologic processes. Consistent with this frequent cell division and cellular replacement, the above-noted tissues are also frequently associated with high prevalence cancers and diseases related to genetic replication errors. Liquid biopsy sampling of fluids containing cells and cellular components derived from the volume of the ductal tissue/organ can be used to screen and surveil for dysplasia, cancer, and abnormalities. Some of these ductal lining systems exit through a common ductal port (e.g., pancreas: duct of Wirsung, prostate: urethra, breast: mammary ducts, etc.), which facilitates the collection of fluid and sampling throughout larger tissue volume of interest (compared with needle biopsy tissue specimens). Unfortunately, the clinical success has been hampered by modest cell counts and sub-clinical sensitivity.

The combination of ultrasound and a microbubble-based contrast agent has been used in an attempt to increase the cell count with liquid biopsy sampling at the common ductal port of the pancreas. For this, the microbubble-based contrast agent is intravenously administered to a subject. When the microbubble-based contrast agent is in a vessel of interest, low pressure amplitude ultrasound waves are directed at the microbubbles, which cause the microbubbles to vibrate, but not burst. The vibrating microbubbles produce pressure waves that traverse the vessel to pancreas tissues. The pressure waves in the pancreas tissues may shorten a shedding time of ductal lining cells that are in the process of being shed, which may increase the cell count at a given moment in time. Unfortunately, microbubble-based contrast agents are intravenously administered, which increases susceptibility to infection. In addition, their use is limited by uptake and wash-out times. Furthermore, they are contraindicated in some patients.

In view of at least the foregoing, there is an unresolved need for an improved approach(s) for facilitating shedding of ductile and/or other tissue lining cells with ultrasound.

SUMMARY

Aspects of the application address the above matters, and others. This summary introduces concepts that are described in more detail in the detailed description. It should not be used to identify essential features of the claimed subject matter, nor to limit the scope of the claimed subject matter.

In one aspect, an ultrasound system includes transmit circuitry configured to produce a push pulse electrical excitation signal. The ultrasound system further includes a transducer array configured to receive the push pulse electrical excitation signal and transmit a push pulse that produces acoustic longitudinal and shear wave propagation in tissue of interest, thereby promoting shedding of lining cells of the tissue of interest in connection with a biopsy of shed cells for the tissue of interest. The push pulse is based on a pre-determined set of parameters stored in computer readable medium.

In one instance(s), the acoustic longitudinal and shear wave propagations increase a number of the shed lining cells of the tissue of interest for the given time period.

In one instance(s), the set of pre-determined parameters include a pulse width in a range of twenty microseconds to five milliseconds.

In one instance(s), the set of pre-determined parameters include a pressure amplitude in a range of fifty kilopascals to five megapascals.

In one instance(s), the transducer array includes more than one transducer element, and the transmit circuitry is further configured to apply time delays to the more than one transducer element to focus the push pulse.

In one instance(s), the acoustic longitudinal and shear wave propagations traverse in-plane of the transducer array.

In one instance(s), the shear wave propagation traverses out-of-plane of the transducer array.

In one instance(s), receive circuitry is configured to receive echo signals produced in response to an interaction of an imaging pressure wave and tissue.

In one instance(s), a beamformer configured to beamform the echo signals, producing an ultrasound image.

In one instance(s), the transmit array is further configured to alternatively transmit the push pulse and the imaging pulse based on a predetermined timing sequence.

In one instance(s), the push pulse promotes the shedding in an absence of microbubbles of a microbubble-based ultrasound contrast agent.

In one instance(s), the set of pre-determined parameters include a combination of a pulse width value and a pressure amplitude value configured to provide a predetermined biologic effect.

In one instance(s), the set of pre-determined parameters includes different combinations of pulse widths and pressure amplitudes for the predetermined biologic effect for different types of tissues.

In one instance(s), the push pulse includes a single pulse.

In one instance(s), the push pulse includes multiple-simultaneous pulses.

In another aspect, a computer-implemented method includes producing a push pulse electrical excitation signal. The computer-implemented method further includes transmitting, based on the push pulse electrical excitation signal, a push pulse that produces acoustic longitudinal and shear wave propagation in tissue of interest, thereby promoting shedding of lining cells of the tissue of interest in connection with a biopsy of shed cells for the tissue of interest.

In one instance(s), the computer-implemented method further includes producing the push pulse electrical excitation signal based on a combination of a pulse width and a pulse pressure amplitude.

In one instance(s), the computer-implemented method further includes producing the push pulse electrical excitation signal based on a pre-determined timing sequence.

In another aspect, a computer readable medium is encoded with computer executable instructions, which, when executed by a processor, cause the processor to perform one or more functions. For example, in one instance(s) the computer executable instructions cause the processor to produce a push pulse electrical excitation signal. In one instance(s) the computer executable instructions further cause the processor to produce a push pulse electrical excitation signal transmit, based on the push pulse electrical excitation signal, a push pulse that produces acoustic longitudinal and shear wave propagation in tissue of interest, thereby promoting shedding of lining cells of the tissue of interest in connection with a biopsy of shed cells for the tissue of interest.

In one instance(s), the push pulse has a frequency in a range of 1.0 to 10 MHz, a pulse width of 2000 cycles or 800 μs, and a peak negative pressure amplitude at 2.5 MHz of 3.0 MPa.

In one instance(s), the computer executable instructions further cause the processor to increase the pulse width and decrease the pressure amplitude or increase the pressure amplitude and decrease the pulse width while maintaining a same biologic effect.

Those skilled in the art will recognize still other aspects of the present application upon reading and understanding the attached description.

BRIEF DESCRIPTION OF THE DRAWINGS

The application is illustrated by way of example and not limited by the figures of the accompanying drawings in which like references indicate similar elements.

DETAILED DESCRIPTION

The human body is made up of cells that renew over time by shedding older cells and replacing them with newly made cells through normal physiologic processes. In some instances, the shed cells provide useful information and can be readily collected, e.g., for screening, etc. For example, and as previously explained herein, ductal lining cells of the pancreas, due to their rapid turn-over rates, are well suited for screening for cancer, etc. and can be readily obtained via liquid biopsy sampling of fluids at a common ductal port of the pancreas. Other shedding cells include endothelial cells and/or tissue with cells that shed.

Described herein is an approach that, in one instance, increases the number of shed cells at a given moment in time by an unforeseen amount, e.g., a couple orders of magnitude relative to the normal physiologic processes. In addition, the approach mitigates intravenous administration of a microbubble contrast agent and the shortcomings therewith. The approach includes generating a push pulse (a narrow focused longitudinal wave with a pressure amplitude and width within in predetermined ranges), which, when applied to shedding tissue, provides local mechanical vibrations, including acoustic radiation pressure and shear wave propagation, which promote cell shedding.

Figure 1:
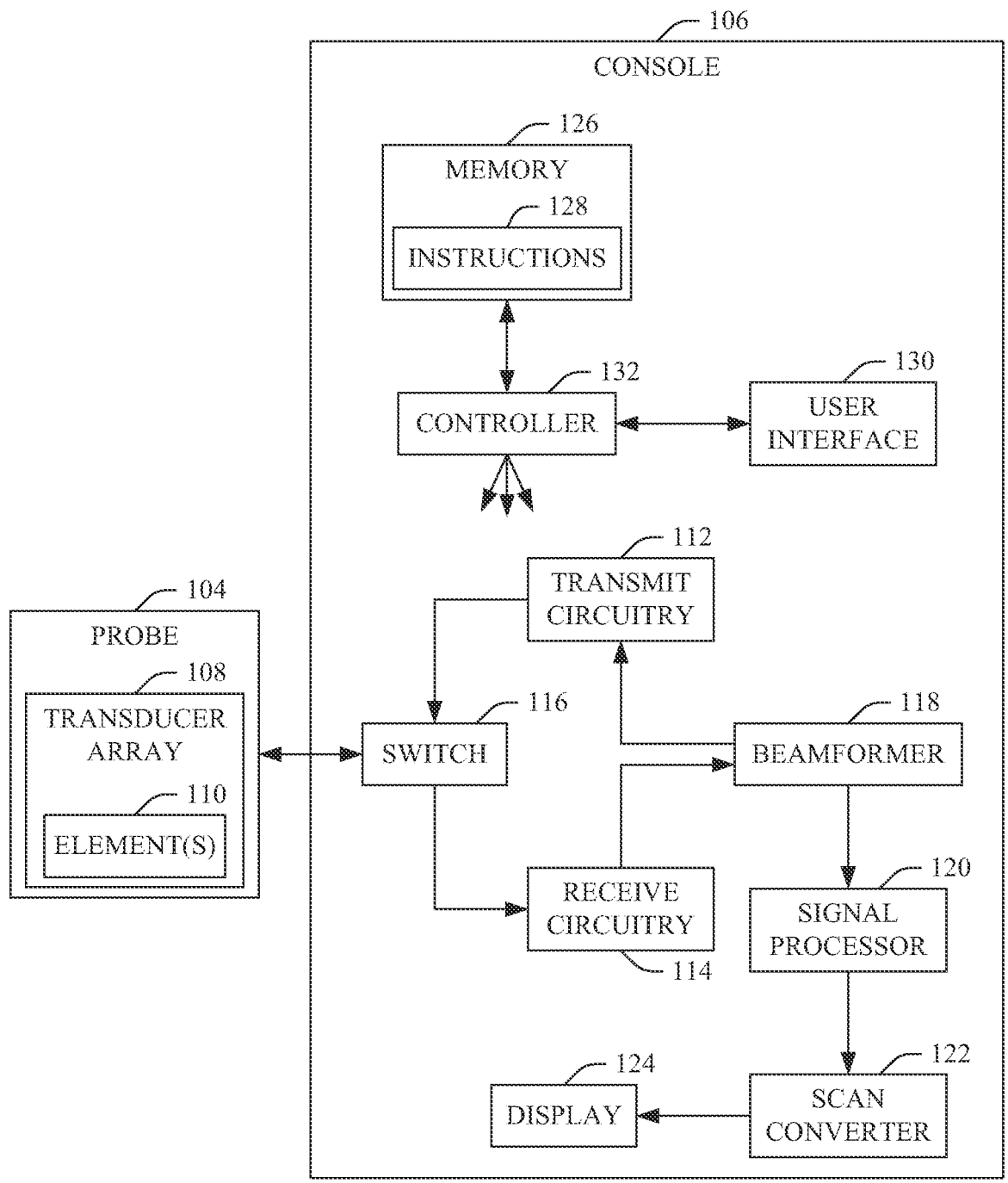
FIG. 1 schematically illustrates a non-limiting example of an ultrasound system, in accordance with an aspect of an embodiment(s) herein.

FIG. 1 schematically illustrates a non-limiting example of an ultrasound system 102. The ultrasound system 102 includes a probe 104 and a console 106. The probe 104 and the console 106 interface with each other through wired and/or wireless technology(s). In another instance, the probe 104 and the console 106 are integrated in a same housing such as part of a hand-held ultrasound system, etc.

The probe 104 includes a transducer array 108 with one or more transducer elements 110. The transducer array 108 includes a one- or two-dimensional, linear, curved and/or otherwise shaped, fully populated or sparse, etc. array. The one or more transducer elements 110 are configured to convert an excitation electrical signal into an ultrasound pressure field. This includes converting a push pulse excitation electrical signal into a push pulse and/or an imaging pulse excitation electrical signal into an imaging pressure field.

As briefly discussed above, and as further described in greater detail below, a push pulse is narrow focused longitudinal wave where the pressure amplitude and pulse width are configured to provide acoustic radiation pressure and shear wave propagation in tissue of interest to promote cell shedding, e.g., in connection with liquid biopsy sampling of shed cells. The imaging pulse is configured for imaging applications include as B-mode, A-mode, elastography, doppler, harmonic, color flow, etc.

The one or more elements 110 are further configured to receive an echo (an ultrasound pressure field) produced in response to the transmitted imaging pressure field interacting with tissue such as ductal, vessel, organ, and/or other tissue. The one or more elements 110 are further configured to convert the echo into an electrical, e.g., radio frequency (RF) signal. The one or more elements 110 are not operated to receive pressure fields produced in response to the push pulse.

The console 106 includes transmit circuitry 112 configured to generate the excitation electrical signal provided to transducer array 108, including the push pulse excitation electrical signal for the push pulse and the imaging pulse excitation electrical signal for the imaging pressure field. The console 106 further includes receive circuitry 114 configured to receive the RF signal generated by the one or more elements 110 of the transducer array 108. The receive circuitry 114 may also be configured to amplify, digitize, focus, and/or otherwise process the signal.

The console 106 further includes a switch 116 configured to switch between the transmit circuitry 112 and the receive circuitry 114, e.g., by electrically connecting the transmit circuitry 112 for a transmit operation and electrically connecting the receive circuitry 114 for a receive operation. In an alternative instance, separate switches are employed for each of the transmit circuitry 112 and the receive circuitry 114.

The console 106 further includes a beamformer 118. For transmit operations, the beamformer 118 is configured to generate delays for individual elements 110 of the transducer array 108, e.g., for transmit focusing, beam steering, etc. For receive operations, the beamformer 118 is configured to beamform, e.g., via delay-and-sum and/or other beamforming, the signals from the receive circuitry 114 and construct a scanplane of scanlines of data.

The console 106 further includes a signal processor 120 configured to perform other processing on the data such as filtering (e.g., via a Finite Impulse Response (FIR) filter, an Infinite Impulse Response (IIR) filter, etc.), time gain compensation (TGC), compression, demodulation and envelope detection, noise rejection, and/or other processing.

The console 106 further includes a scan converter 122 and a display 124. The scan converter 122 scan converts the processed signal into the coordinate system of the display 124. The scan converter 122 can be configured to employ analog and/or digital scan converting techniques. The scan converted data can be displayed on the display 124 and/or other display monitor.

The console 106 further includes computer readable medium ("memory") 126, which includes non-transitory medium and excludes transitory medium such as signals, carrier waves, and the like). The computer readable medium 126 includes computer readable instructions 128. As described in greater detail below, in one instance, the computer readable instructions 128 includes instructions for different mode of operations and timing diagrams in connection with applying a push pulse(s) to promote cell shedding and/or an imaging pulse to image tissue.

The console 106 further includes a user interface (UI) 130. The user interface 130 includes one or more input devices such as a button, a knob, a slider, a touch screen, a mouse, a keyboard, etc.). The UI 130 allows a user to control an operation of the system 102. For example, in one instance, the UI 130 receives a input indicative of a user selected mode of operation (push pule, imaging, push pulse/imaging, etc.), a push pulse timing scheme for push pulse mode, an imaging parameter, a display parameter, etc.

The console 106 further includes a controller 132. The controller 132 is configured to control one or more of the transmit circuitry 112, the receive circuitry 114, the switch 116, the beamformer 118, the signal processor 120, the scan converter 122 and/or the display 124. For example, in one instance, the controller 132 controls the transmit circuitry 112 to provide a push pulse excitation signal to the transducer 108 based on a selected mode of operation. The controller 132 includes a processor(s) such as a microprocessor, a central processing unit (CPU), etc., which is configured to execute the instructions 128.

As briefly discussed herein, a push pulse includes a pressure amplitude and a pulse width (which is also referred to as a length or a duration) configured to provide acoustic radiation pressure and shear wave propagation in tissue of interest to promote cell shedding. Briefly turning to FIG. 2, a non-limiting example of a push pulse 202 is illustrated. The push pulse 202 has a transmit pressure amplitude ("A") 204 in a range of fifty kilopascals (50 kPa) to 5 megapascal (5 MPa) and a width ("τ") 206 in a range of twenty microseconds (20 µs) to five milliseconds (5 ms). The transmit pressure amplitude has an index of cavitation/Mechanical Index (MI) in a range of 0.2 to 6.0 such as <1.9, consistent with diagnostic imaging guidelines. Other values for A, τ and/or MI, including greater and/or smaller, are contemplated herein.

In general, the push pulse displaces tissue axially along the beam and shear restoring force induces transverse-mode wave to propagate radially, in three-dimensions. In one instance, one combination of transmit pressure amplitude and pulse width may be better suited for one particular tissue type, while another combination of transmit pressure amplitude and pulse width may be better suited for another tissue type. For example, different tissues have different stiffness and/or are located at different depths. As such, the different combinations can be tuned to the different tissue types. In one instance, the pressure amplitude and pulse width are set within middle portions of their respective ranges, where an equivalent biologic effect can be achieved with a balance of a higher amplitude and a shorter pulse width or a lower amplitude and a longer pulse width.

For a simple 1-D (plane wave) approximation, the acoustic radiation force can be determined by $$F = \frac{2\alpha I}{c_0},$$

where F represents radiation force in a unit of kilogram per seconds squared per centimeter squared (kg/(s$^2$ cm$^2$), I represents an average temporal intensity at a given point in a unit of watt per centimeter squared (W/cm$^2$), α represents an attenuation coefficient in a unit of Neper per centimeter (Np/cm), and co represents the speed of sound in a unit of centimeter per second (cm/s). The amount ductal lining cell shedding is expected to scale with the radiation force (F), which is linearly dependent on the average temporal intensity (I), which is proportional to the pressure amplitude squared (I∝A$^2$) and linearly scales with the pulse width (I∝τ).

Figure 3:
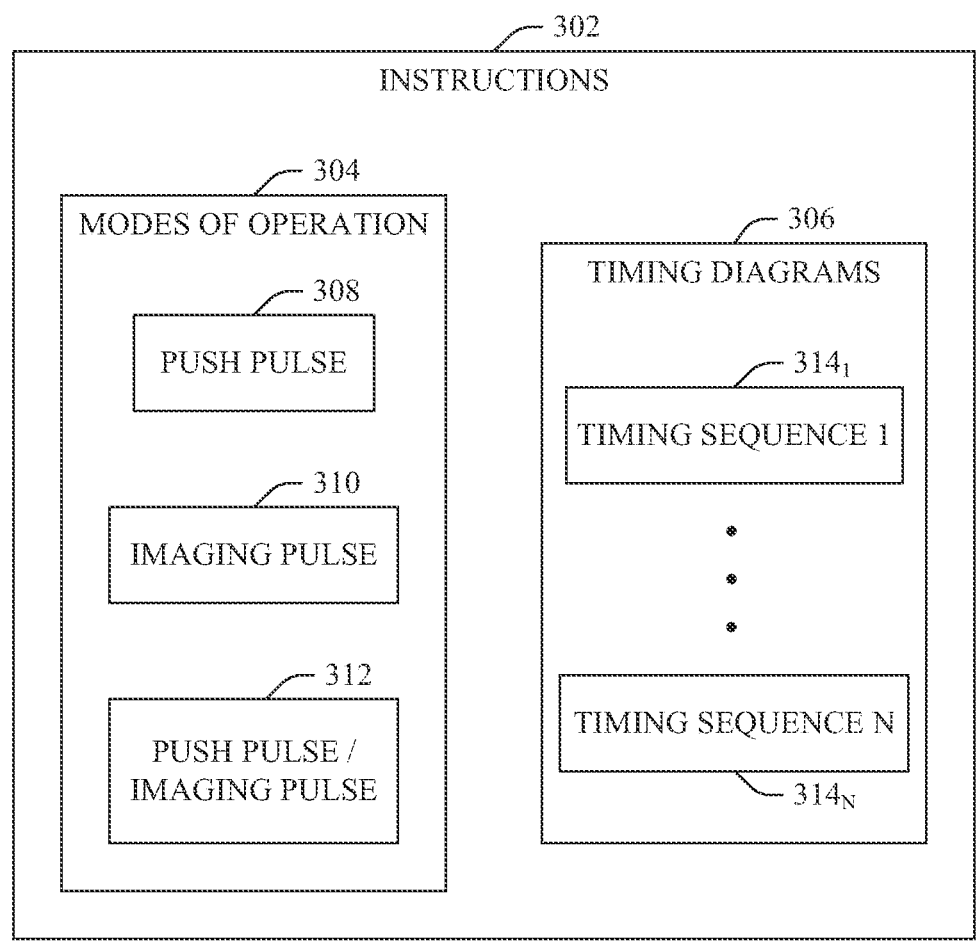
FIG. 3 schematically illustrates a non-limiting example of instructions, including modes of operation and timing diagrams, in accordance with an aspect of an embodiment(s) herein.

Returning to FIG. 1, as briefly discussed herein, the memory 126 includes the instructions 128 for a mode of operation and a timing diagram. Briefly turning to FIG. 3, a non-limiting example of instructions 302 of the instructions 128 are illustrated. The instructions 302 includes modes of operation 304 and timing diagrams 306.

The modes of operation 304 includes a push pulse mode 308, an imaging pulse mode 310 and a push pulse/imaging pulse 312 mode. In the push pulse mode 308, only push pulses are generated. In the imaging pulse mode 310, only imaging pulses are generated. In the push pulse/imaging pulse mode 312, both push pulses and imaging pulses are generated.

The timing diagrams 306 include timing a first timing sequence 314$_1$, . . . , and an Nth timing sequence 314$_N$, where N is an integer equal to or greater than one. Collectively, the first timing sequence 314$_1$, . . . , and the Nth timing sequence 314$_N$ are also referred to as timing sequences 314. Each of the timing sequences 314 includes a timing sequence for a push pulse and/or an imaging pulse.

Figure 4:
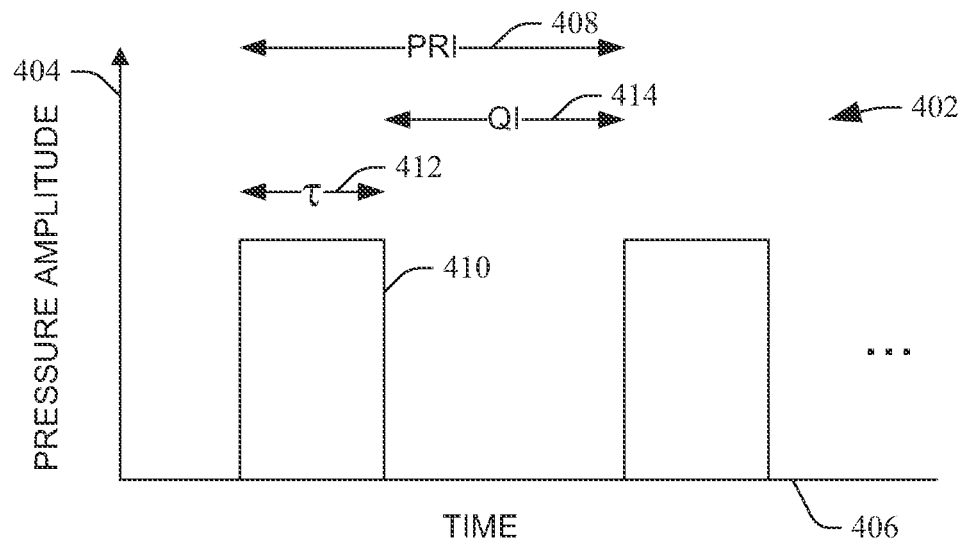
FIG. 4 schematically illustrates a non-limiting example of a timing scheme, in accordance with an aspect of an embodiment(s) herein.

Briefly turning to FIG. 4, a non-limiting example of a timing sequence 402 of the timing sequences 314 for the push pulse/imaging pulse mode 312 is illustrated. A first axis 404 represents transmit pressure amplitude and a second axis 406 represents time. The timing sequence 402 includes a pulse repetition frequency interval (PRI) 408, which includes a single pulse 410 with the pulse width (τ) 412 and a quiescence interval (QI) 414.

The PRI is in a range of 500 µs to five seconds (5 s). As such, a pulse repetition frequency (PRF) is in a range of two kilohertz (2 kHz) to 0.2 Hz. As discussed above in connection with FIG. 2, the transmit pressure amplitude is in the range of 50 kPa-5 MPa and the pulse (i) 206 in the range of 20 µs-5 ms. Imaging frames are acquired during the quiescence interval 414. For example, standard imaging frames may be interleaved and acquired during the quiescence interval 414 to maintain anatomic positioning and targeting of push pulses.

Table 1 below shows a non-limiting example of transmit pulse characteristics for both a push pulse and an imaging pulse. From Table 1, the ultrasound frequency range for the push pulse is in a range of 1.0 to 10 MHz, the ultrasound frequency range for the imaging pulse is in a range of 1.0 to 20 MHz, and, for an abdominal procedure, an example ultrasound frequency for the push pulse and for the imaging pulse is 2.5 MHz. From Table 1, an example pulse width of the push pulse is 2000 cycles or 800 µs, and an example pulse width of the imaging pulse is 1-2 cycles or 0.5 µs. From Table 1, an example peak negative pressure amplitude at 2.5 MHz for the push pulse is less than 3.6 MPa (e.g., 3.0 MPa), and an example peak negative pressure amplitude at 2.5 MHz for the imaging pulse is less than 3.6 MPa (e.g., 2.6 MPa). From Table 1, an example MI for the push pulse is less than 1.9 (e.g., 1.6), and an example MI for the imaging pulse is less than 1.9 (e.g., 1.4),

TABLE 1

Non-limiting example of transmit push pulse and imaging pulse characteristics.

| | Push Pulse | Imaging Pulse |
|---|---|---|
| Ultrasound Frequency Range | 1.0-10 MHz | 1.0-20 MHz |
| Example Abdominal Ultrasound Frequency | 2.5 MHz | 2.5 MHz |
| Pulse Width (cycles) | 2000 cycles | 1-2 cycles |
| Pulse Width (seconds) | 800 µs | 0.5 µs |
| Peak Negative Pressure Amplitude (Pa) @ 2.5 MHz | <3.6 MPa (e.g., 3.0 MPa) | <3.6 MPa (e.g., 2.6 MPa) |
| Mechanical Index (MI) | <1.9 (e.g., 1.6) | <1.9 (e.g., 1.4 for diagnostic imaging) |

Figure 5:
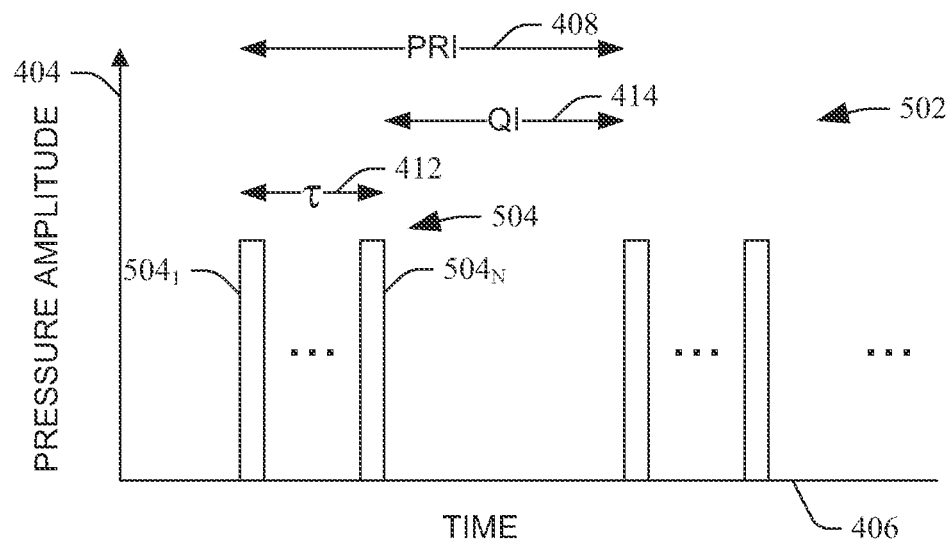
FIG. 5 schematically illustrates another non-limiting example of a timing scheme, in accordance with an aspect of an embodiment(s) herein.

Briefly turning to FIG. 5, a non-limiting example of another timing sequence 502 for the push pulse/imaging pulse mode 312 is illustrated. The timing sequence 502 is similar to the timing sequence 402 of FIG. 4, with the exception that instead of transmitting the single pulse 410 each PRI 408, the timing sequence 502 includes a set of two or more pulses $504_1, \ldots, 504_N$, where N is an integer greater than one, that are sequentially transmitted. Collectively, the set of two or more pulses $504_1, \ldots, 504_N$ are also referred to herein as pulses 504.

Figure 6:
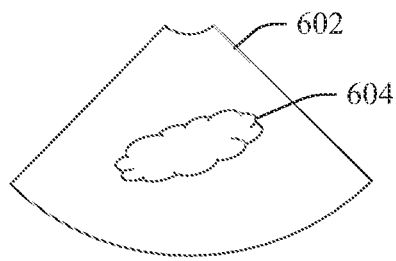
FIGS. 6, 7 and 8 graphically illustrate an example flow of a process, in accordance with an aspect of an embodiment(s) herein.
Figure 7:
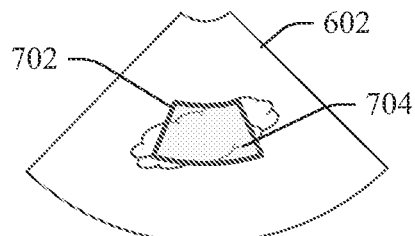
Figure 8:
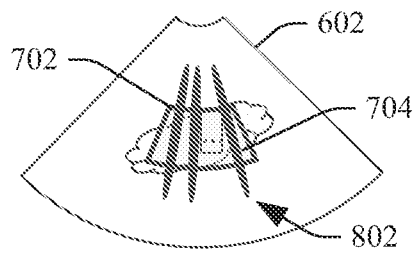

FIGS. 6, 7 and 8 graphically illustrates flow from identifying ductal tissue structure of interest with an imaging pulse to applying a push pulse. Initially referring to FIG. 6, an image 602 of an anatomy 604 is acquired to identify tissue for a shed cell biopsy. The image can be acquired with the imaging system 102 and/or other imaging system. Turning to FIG. 7, a region of interest (ROI) 702 is placed over the image 602, bounding ductal tissue structure of interest 704 for targeting a push pressure pulse(s) based on anatomic information. The ROI 702 can be created and placed via manually by a user, automated with an algorithm, or a combination thereof.

Turning to FIG. 8, a set of push pulses 802 are applied to the ductal tissue structure of interest 704 bounded by the ROI 702 in the image 602. In one instance(s), the set of push pulses 802 includes multiple-simultaneous pulses. In another instance(s), the set of push pulses 802 includes a single pulse. In another instance(s), the set of push pulses 802 includes sequential pulses. Images can be generated during the quiescence intervals 414, as described herein, and utilized to maintain and/or reposition the transducer array 108 with respect to the ductal tissue structure of interest. After the application of the push pulse(s), the biopsy can be performed.

FIGS. 4, 5, 6, 7 and 8 are directed to the push pulse/imaging pulse mode 312. For the push pulse mode 308, only a push pulse(s), and not an imaging pulse(s), is transmitted. For the imaging pulse mode 310, only an imaging pulse(s), and not a push pulse(s), is transmitted.

Figure 9:
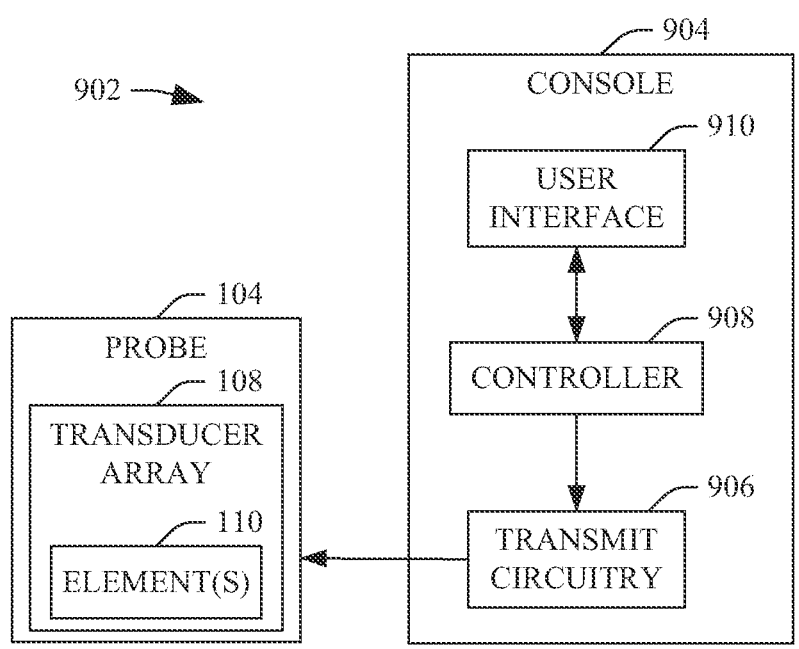
FIG. 9 schematically illustrates another non-limiting example of an ultrasound system, in accordance with an aspect of an embodiment(s) herein.

FIG. 9 schematically illustrates an example ultrasound system 902, which is a variation of the example ultrasound system 102 described in connection with FIG. 1. In another variation, the probe 104 and the console 904 are integrated in a same housing such as part of a hand-held ultrasound system. In general, the ultrasound system 902 is not configured for generating images; the ultrasound system 902 is configured only for generating push pulses.

The ultrasound system 902 includes the probe 104 and a console 904, which interface with each other through wired and/or wireless technology(s). The console 904 includes a transmitter circuitry 906, a controller 908 and a user interface 910. The transmitter circuitry 906, the controller 908 and the user interface 910 are substantially similar to the transmitter 112, the controller 132 and the user interface 130. The ultrasound system 902 can be employed alone or in connection with an imaging device.

Figure 10:
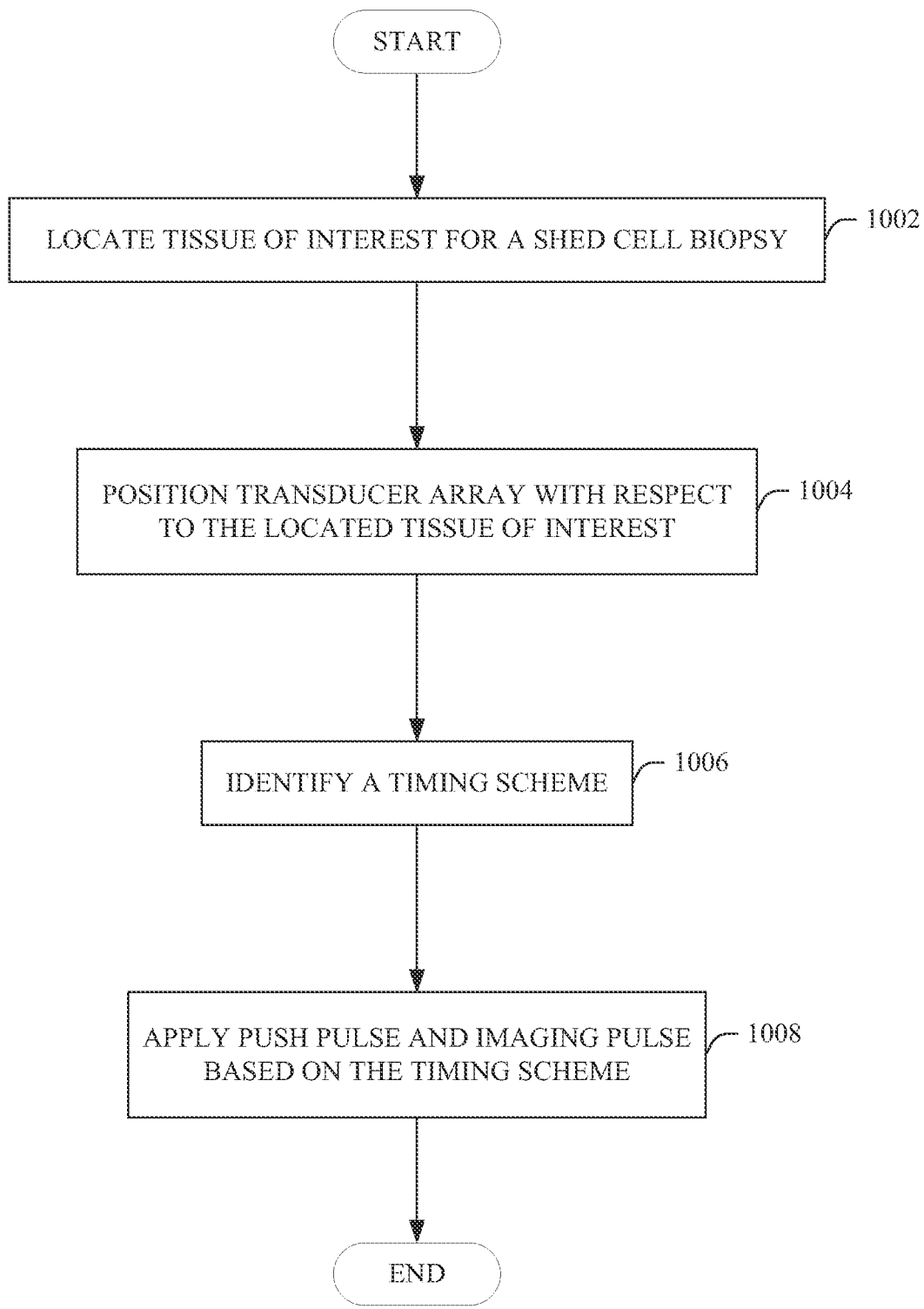
FIG. 10 illustrates a non-limiting example of a flow chart for a computer-implemented method, in accordance with an embodiment(s) herein.

FIG. 10 illustrates a non-limiting example of a flow chart for a computer-implemented method. It is to be appreciated that the ordering of the acts in the method is not limiting. As such, other orderings are contemplated herein. In addition, one or more acts may be omitted, and/or one or more additional acts may be included.

At 1002, tissue of interest for a shed cell biopsy is located, as discussed herein and/or otherwise. For example, an ultrasound image of anatomy is acquired. A region(s) of interest (ROI) is then placed over the image to bounds ductal tissue structure(s) of interest for targeting a push pressure pulse(s) based on anatomic information. The ROI can be created and placed via manually by a user, automated with an algorithm, or a combination thereof. At 1004, a transducer array is positioned with respect to the tissue of interest, as discussed herein and/or otherwise.

At 1006, a timing scheme of the timing schemes for the push pulse/imaging pulse mode is selected, as discussed herein and/or otherwise. As discussed herein, the system 102 may be configured with one or more modes of operation, including a push pulse mode, an imaging pulse mode and a push pulse/imaging pulse mode. In the push pulse mode only push pulses are generated, in the imaging pulse mode only imaging pulses are generated, an in the push pulse/imaging pulse mode both push pulses and imaging pulses are generated. The present example describes push pulse/imaging pulse mode.

Figure 2:
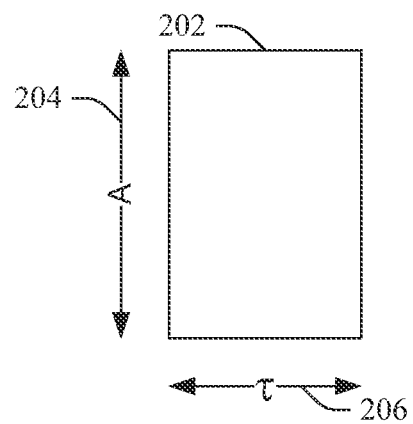
FIG. 2 schematically illustrates a non-limiting example of a push pulse, in accordance with an aspect of an embodiment(s) herein.

FIG. 4 describes a non-limiting example of the timing sequence 402 of the timing sequences 314 for the push pulse/imaging pulse mode 312. The timing sequence 402 indicates transmit pressure amplitude versus time and includes the PRI 408, which includes the single pulse 410 with the pulse width 412 and the quiescence interval 414. Again, the PRI is in the range of 500 µs to 5 µs, and, as such, the PRF is in the range of 2 kHz to 0.2 Hz. FIG. 2 describes the transmit pressure amplitude with the range of 50 kPa-5 MPa and the pulse 206 in the range of 20 μs-5 ms. FIG. 5 describes another timing sequence 502 for the push pulse/imaging pulse mode 312.

Table 1 shows a non-limiting example of transmit pulse characteristics for both a push pulse and an imaging pulse. From Table 1, the ultrasound frequency range for the push pulse is in a range of 1.0 to 10 MHz, the ultrasound frequency range for the imaging pulse is in a range of 1.0 to 20 MHz, and, for an abdominal procedure, an example ultrasound frequency for the push pulse and for the imaging pulse is 2.5 MHz. From Table 1, an example pulse width of the push pulse is 2000 cycles or 800 μs, and an example pulse width of the imaging pulse is 1-2 cycles or 0.5 μs. From Table 1, an example peak negative pressure amplitude at 2.5 MHz for the push pulse is less than 3.6 MPa, and an example peak negative pressure amplitude at 2.5 MHz for the imaging pulse is less than 3.6 MPa. From Table 1, an example MI for the push pulse is less than 1.9, and an example MI for the imaging pulse is less than 1.9.

At 1008, a push pulse(s) is applied to the tissue of interest and images are generated based on the timing scheme. FIG. 8 shows the set of push pulses 802 applied to the ductal tissue structure of interest 704 bounded by the ROI 702 in the image 602. Again, the set of push pulses 802 may include a single pulse, multiple-simultaneous pulses and/or sequential pulses. Images can be generated during the quiescence intervals 414, as described herein, and utilized to maintain and/or reposition the transducer array 108 with respect to the ductal tissue structure of interest. In another instance, images can be generated during a different interval(s). After the application of the push pulse(s), the biopsy can be performed.

As discussed herein, the human body is made up of cells that renew over time by shedding older cells and replacing them with newly made cells through normal physiologic processes, and, in some instances, the shed cells provide useful information and can be readily collected, e.g., for screening, etc., e.g., and as previously explained herein, ductal lining cells of the pancreas (and/or other shedding cells such as endothelial cells, etc.), due to their rapid turn-over rates, are well suited for screening for cancer, etc. and can be readily obtained via liquid biopsy sampling of fluids at a common ductal port of the pancreas.

The above method, in one instance, increases the number of shed cells at a given moment in time by an unforeseen amount, e.g., a couple orders of magnitude relative to the normal physiologic processes. In addition, the approach mitigates intravenous administration of a microbubble contrast agent and the shortcomings therewith. The method includes generating a push pulse (a narrow focused longitudinal wave with a pressure amplitude and width within in predetermined ranges), which, when applied to shedding tissue, provides local mechanical vibrations, including acoustic radiation pressure and shear wave propagation, which promote cell shedding.

Figure 11:
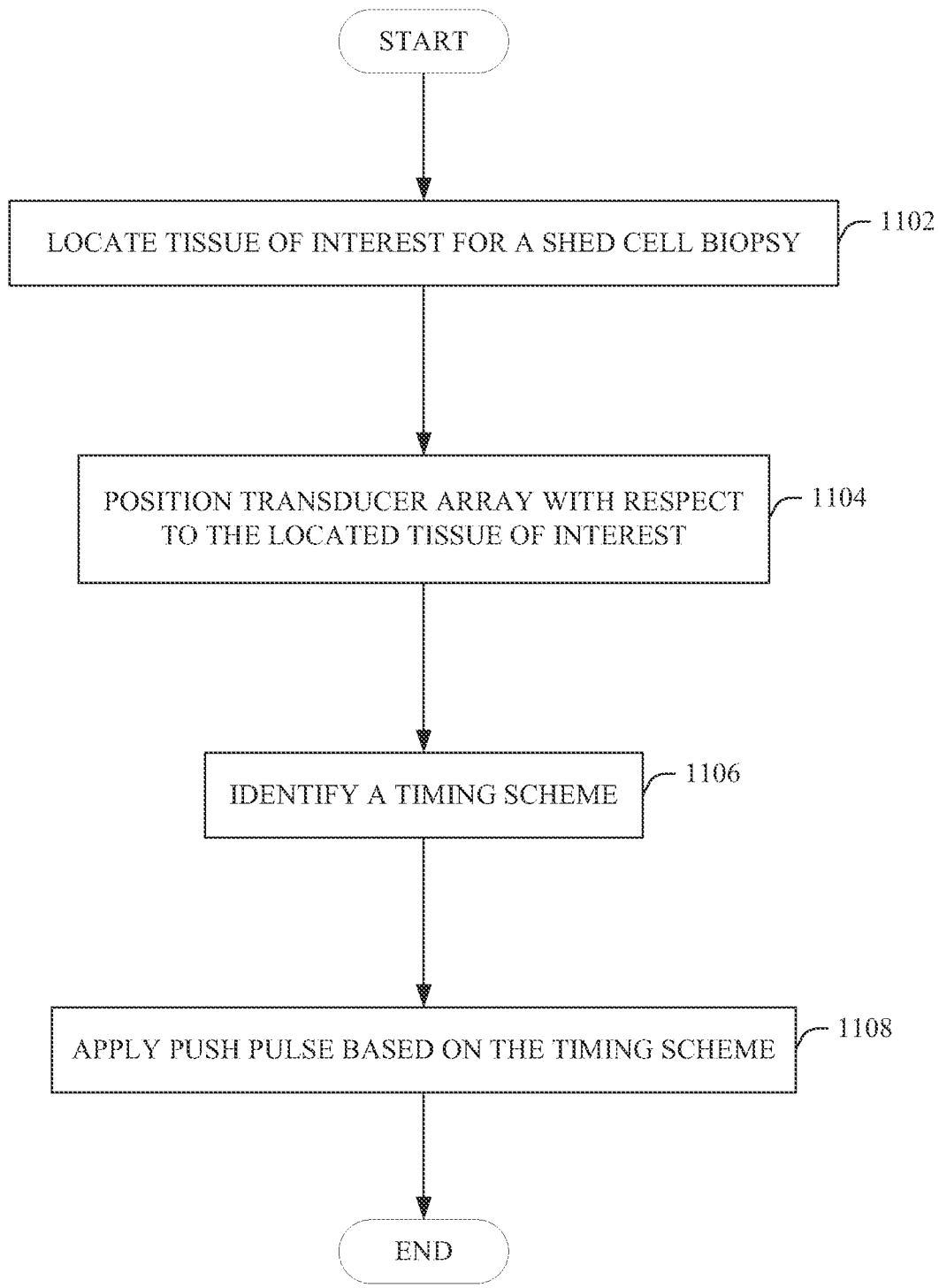
FIG. 11 illustrates another non-limiting example of a flow chart for a computer-implemented method, in accordance with an embodiment(s) herein.

FIG. 11 illustrates a non-limiting example of a flow chart for a computer-implemented method. It is to be appreciated that the ordering of the acts in the method is not limiting. As such, other orderings are contemplated herein. In addition, one or more acts may be omitted, and/or one or more additional acts may be included.

At 1102, tissue of interest for a shed cell biopsy is located, as discussed herein and/or otherwise. For example, an ultrasound image of anatomy is acquired. A region(s) of interest (ROI) is then placed over the image to bounds ductal tissue structure(s) of interest for targeting a push pressure pulse(s) based on anatomic information. The ROI can be created and placed via manually by a user, automated with an algorithm, or a combination thereof. At 1104, a transducer array is positioned with respect to the tissue of interest, as discussed herein and/or otherwise.

At 1106, a timing scheme of the timing schemes for the push pulse mode is selected, as discussed herein and/or otherwise. As discussed herein, the system 102 may be configured with one or more modes of operation, including a push pulse mode, an imaging pulse mode and a push pulse/imaging pulse mode. In the push pulse mode only push pulses are generated, in the imaging pulse mode only imaging pulses are generated, an in the push pulse/imaging pulse mode both push pulses and imaging pulses are generated. The present example describes push pulse mode.

Table 1 shows a non-limiting example of transmit pulse characteristics for a push pulse. From Table 1, the ultrasound frequency range for the push pulse is in a range of 1.0 to 10 MHz, and, for an abdominal procedure, an example ultrasound frequency for the push pulse is 2.5 MHz. From Table 1, an example pulse width of the push pulse is 2000 cycles or 800 μs. From Table 1, an example peak negative pressure amplitude at 2.5 MHz for the push pulse is less than 3.6 MPa. From Table 1, an example MI for the push pulse is less than 1.9.

At 1108, a push pulse(s) is applied to the tissue of interest and images are generated based on the timing scheme. FIG. 8 shows the set of push pulses 802 applied to the ductal tissue structure of interest 704 bounded by the ROI 702 in the image 602. Again, the set of push pulses 802 may include a single pulse, multiple-simultaneous pulses and/or sequential pulses. After the application of the push pulse(s), the biopsy can be performed.

As discussed herein, the human body is made up of cells that renew over time by shedding older cells and replacing them with newly made cells through normal physiologic processes, and, in some instances, the shed cells provide useful information and can be readily collected, e.g., for screening, etc., e.g., and as previously explained herein, ductal lining cells of the pancreas (and/or other shedding cells such as endothelial cells, etc.), due to their rapid turn-over rates, are well suited for screening for cancer, etc. and can be readily obtained via liquid biopsy sampling of fluids at a common ductal port of the pancreas.

The above method, in one instance, increases the number of shed cells at a given moment in time by an unforeseen amount, e.g., a couple orders of magnitude relative to the normal physiologic processes. In addition, the approach mitigates intravenous administration of a microbubble contrast agent and the shortcomings therewith. The method includes generating a push pulse (a narrow focused longitudinal wave with a pressure amplitude and width within in predetermined ranges), which, when applied to shedding tissue, provides local mechanical vibrations, including acoustic radiation pressure and shear wave propagation, which promote cell shedding.

Figure 12:
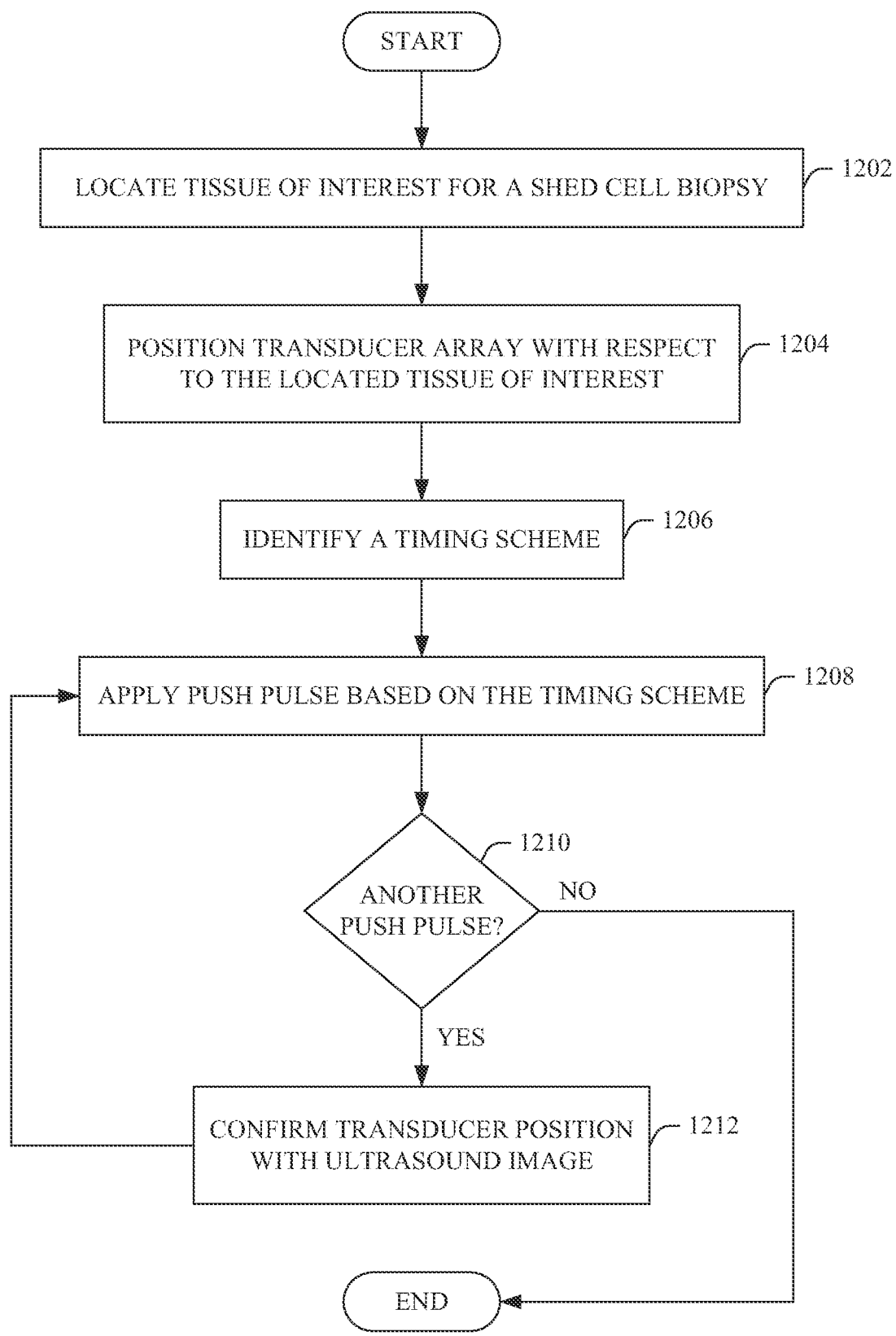
FIG. 12 illustrates another non-limiting example of a flow chart for a computer-implemented method, in accordance with an embodiment(s) herein.

FIG. 12 illustrates a non-limiting example of a flow chart for a computer-implemented method. It is to be appreciated that the ordering of the acts in the method is not limiting. As such, other orderings are contemplated herein. In addition, one or more acts may be omitted, and/or one or more additional acts may be included.

At 1202, tissue of interest for a shed cell biopsy is located, as discussed herein and/or otherwise. For example, an ultrasound image of anatomy is acquired. A region(s) of interest (ROI) is then placed over the image to bounds ductal tissue structure(s) of interest for targeting a push pressure pulse(s) based on anatomic information. The ROI can be created and placed via manually by a user, automated with an algorithm, or a combination thereof. At 1204, a transducer array is positioned with respect to the tissue of interest, as discussed herein and/or otherwise.

At 1206, a timing scheme of the timing schemes for the push pulse/imaging pulse mode is selected, as discussed herein and/or otherwise. As discussed herein, the system 102 may be configured with one or more modes of operation, including a push pulse mode, an imaging pulse mode and a push pulse/imaging pulse mode. In the push pulse mode only push pulses are generated, in the imaging pulse mode only imaging pulses are generated, an in the push pulse/imaging pulse mode both push pulses and imaging pulses are generated. The present example describes push pulse/imaging pulse mode.

FIG. 4 describes a non-limiting example of the timing sequence 402 of the timing sequences 314 for the push pulse/imaging pulse mode 312. The timing sequence 402 indicates transmit pressure amplitude versus time and includes the PRI 408, which includes the single pulse 410 with the pulse width 412 and the quiescence interval 414. Again, the PRI is in the range of 500 μs to 5 μs, and, as such, the PRF is in the range of 2 kHz to 0.2 Hz. FIG. 2 describes the transmit pressure amplitude with the range of 50 kPa-5 MPa and the pulse 206 in the range of 20 μs-5 ms. FIG. 5 describes another timing sequence 502 for the push pulse/imaging pulse mode 312.

Table 1 shows a non-limiting example of transmit pulse characteristics for both a push pulse and an imaging pulse. From Table 1, the ultrasound frequency range for the push pulse is in a range of 1.0 to 10 MHz, the ultrasound frequency range for the imaging pulse is in a range of 1.0 to 20 MHz, and, for an abdominal procedure, an example ultrasound frequency for the push pulse and for the imaging pulse is 2.5 MHz. From Table 1, an example pulse width of the push pulse is 2000 cycles or 800 μs, and an example pulse width of the imaging pulse is 1-2 cycles or 0.5 μs. From Table 1, an example peak negative pressure amplitude at 2.5 MHz for the push pulse is less than 3.6 MPa, and an example peak negative pressure amplitude at 2.5 MHz for the imaging pulse is less than 3.6 MPa. From Table 1, an example MI for the push pulse is less than 1.9, and an example MI for the imaging pulse is less than 1.9.

At 1208, a push pulse(s) is applied to the tissue of interest and images are generated based on the timing scheme. FIG. 8 shows the set of push pulses 802 applied to the ductal tissue structure of interest 704 bounded by the ROI 702 in the image 602. Again, the set of push pulses 802 may include a single pulse, multiple-simultaneous pulses and/or sequential pulses. At 1210, it is determined if another push pulse(s) is to be applied. This information may be part of the timing sequence, the protocol, user determined, etc. If it is determined that another push pulse will not be applied, the biopsy can then be performed.

If it is determined that another push pulse(s) will be applied, at 1212 images can be generated with data acquired during the quiescence intervals 414, as described herein, and utilized to maintain and/or reposition the transducer array 108 with respect to the ductal tissue structure of interest. In another instance, images can be generated during a different interval. Then, the steps 1208 and 1210 are then repeated until it is determined that another push pulse will not be applied. The biopsy can then be performed.

As discussed herein, the human body is made up of cells that renew over time by shedding older cells and replacing them with newly made cells through normal physiologic processes, and, in some instances, the shed cells provide useful information and can be readily collected, e.g., for screening, etc., e.g., and as previously explained herein, ductal lining cells of the pancreas (and/or other shedding cells such as endothelial cells, etc.), due to their rapid turn-over rates, are well suited for screening for cancer, etc. and can be readily obtained via liquid biopsy sampling of fluids at a common ductal port of the pancreas.

The above method, in one instance, increases the number of shed cells at a given moment in time by an unforeseen amount, e.g., a couple orders of magnitude relative to the normal physiologic processes. In addition, the approach mitigates intravenous administration of a microbubble contrast agent and the shortcomings therewith. The method includes generating a push pulse (a narrow focused longitudinal wave with a pressure amplitude and width within in predetermined ranges), which, when applied to shedding tissue, provides local mechanical vibrations, including acoustic radiation pressure and shear wave propagation, which promote cell shedding.

Figure 13:
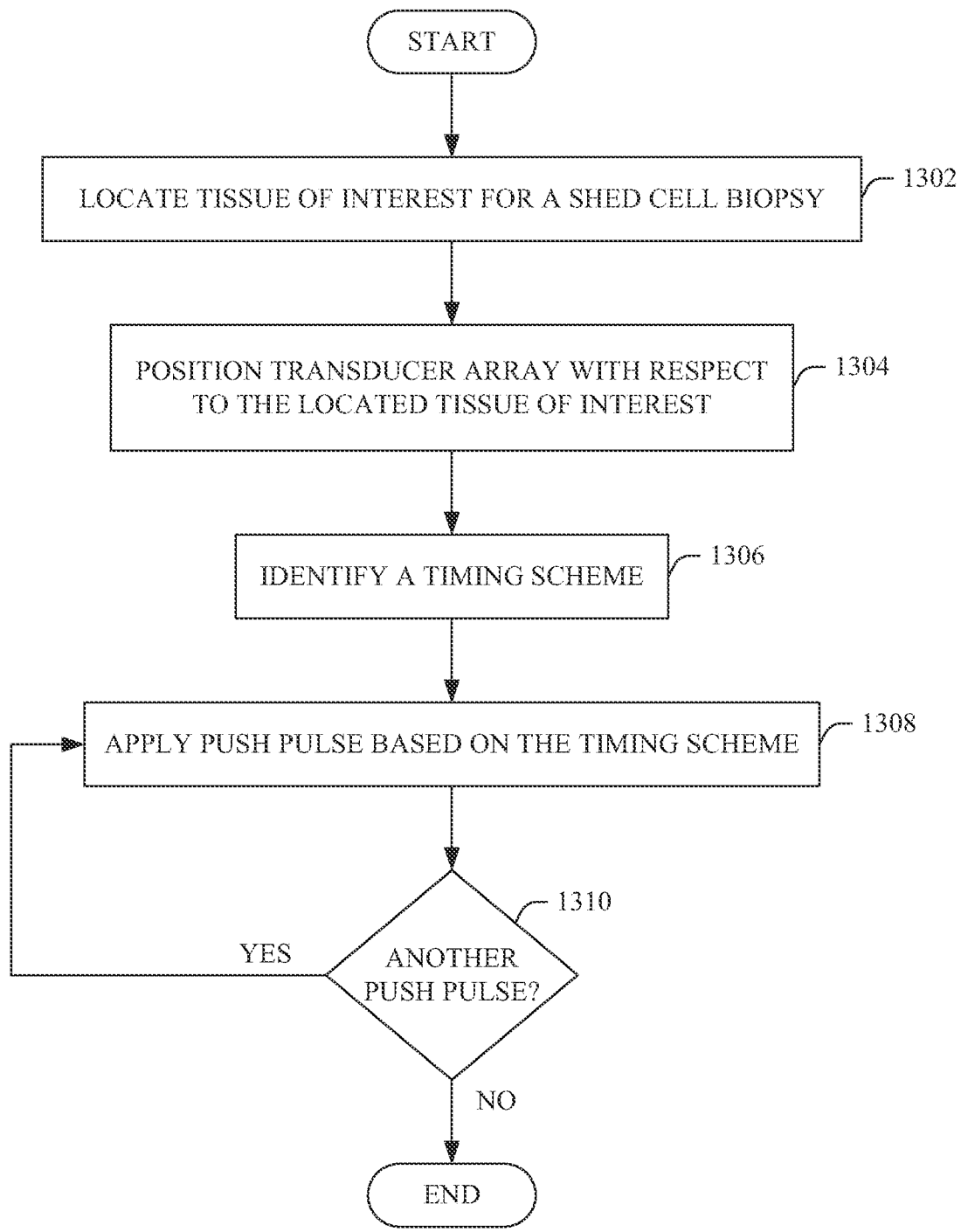
FIG. 13 illustrates another non-limiting example of a flow chart for a computer-implemented method, in accordance with an embodiment(s) herein.

FIG. 13 illustrates a non-limiting example of a flow chart for a computer-implemented method. It is to be appreciated that the ordering of the acts in the method is not limiting. As such, other orderings are contemplated herein. In addition, one or more acts may be omitted, and/or one or more additional acts may be included.

At 1302, tissue of interest for a shed cell biopsy is located, as discussed herein and/or otherwise. For example, an ultrasound image of anatomy is acquired. A region(s) of interest (ROI) is then placed over the image to bounds ductal tissue structure(s) of interest for targeting a push pressure pulse(s) based on anatomic information. The ROI can be created and placed via manually by a user, automated with an algorithm, or a combination thereof. At 1304, a transducer array is positioned with respect to the tissue of interest, as discussed herein and/or otherwise.

At 1306, a timing scheme of the timing schemes for the push pulse mode is selected, as discussed herein and/or otherwise. As discussed herein, the system 102 may be configured with one or more modes of operation, including a push pulse mode, an imaging pulse mode and a push pulse/imaging pulse mode. In the push pulse mode only push pulses are generated, in the imaging pulse mode only imaging pulses are generated, an in the push pulse/imaging pulse mode both push pulses and imaging pulses are generated. The present example describes push pulse mode.

Table 1 shows a non-limiting example of transmit pulse characteristics for a push pulse. From Table 1, the ultrasound frequency range for the push pulse is in a range of 1.0 to 10 MHz, and, for an abdominal procedure, an example ultrasound frequency for the push pulse is 2.5 MHz. From Table 1, an example pulse width of the push pulse is 2000 cycles or 800 μs. From Table 1, an example peak negative pressure amplitude at 2.5 MHz for the push pulse is less than 3.6 MPa. From Table 1, an example MI for the push pulse is less than 1.9.

At 1308, a push pulse(s) is applied to the tissue of interest and images are generated based on the timing scheme. FIG. 8 shows the set of push pulses 802 applied to the ductal tissue structure of interest 704 bounded by the ROI 702 in the image 602. Again, the set of push pulses 802 may include a single pulse, multiple-simultaneous pulses and/or sequential pulses.

At 1310, it is determined if another push pulse is to be applied. This information may be part of the timing sequence, the protocol, user determined, etc. If it is determined that another push pulse will not be applied, the biopsy can then be performed. If it is determined that another push pulse(s) will be applied, then the steps 1308 and 1310 are then repeated until it is determined that another push pulse will not be applied. The biopsy can then be performed.

As discussed herein, the human body is made up of cells that renew over time by shedding older cells and replacing them with newly made cells through normal physiologic processes, and, in some instances, the shed cells provide useful information and can be readily collected, e.g., for screening, etc., e.g., and as previously explained herein, ductal lining cells of the pancreas (and/or other shedding cells such as endothelial cells, etc.), due to their rapid turn-over rates, are well suited for screening for cancer, etc. and can be readily obtained via liquid biopsy sampling of fluids at a common ductal port of the pancreas.

The above method, in one instance, increases the number of shed cells at a given moment in time by an unforeseen amount, e.g., a couple orders of magnitude relative to the normal physiologic processes. In addition, the approach mitigates intravenous administration of a microbubble contrast agent and the shortcomings therewith. The method includes generating a push pulse (a narrow focused longitudinal wave with a pressure amplitude and width within in predetermined ranges), which, when applied to shedding tissue, provides local mechanical vibrations, including acoustic radiation pressure and shear wave propagation, which promote cell shedding.

Figure 14:
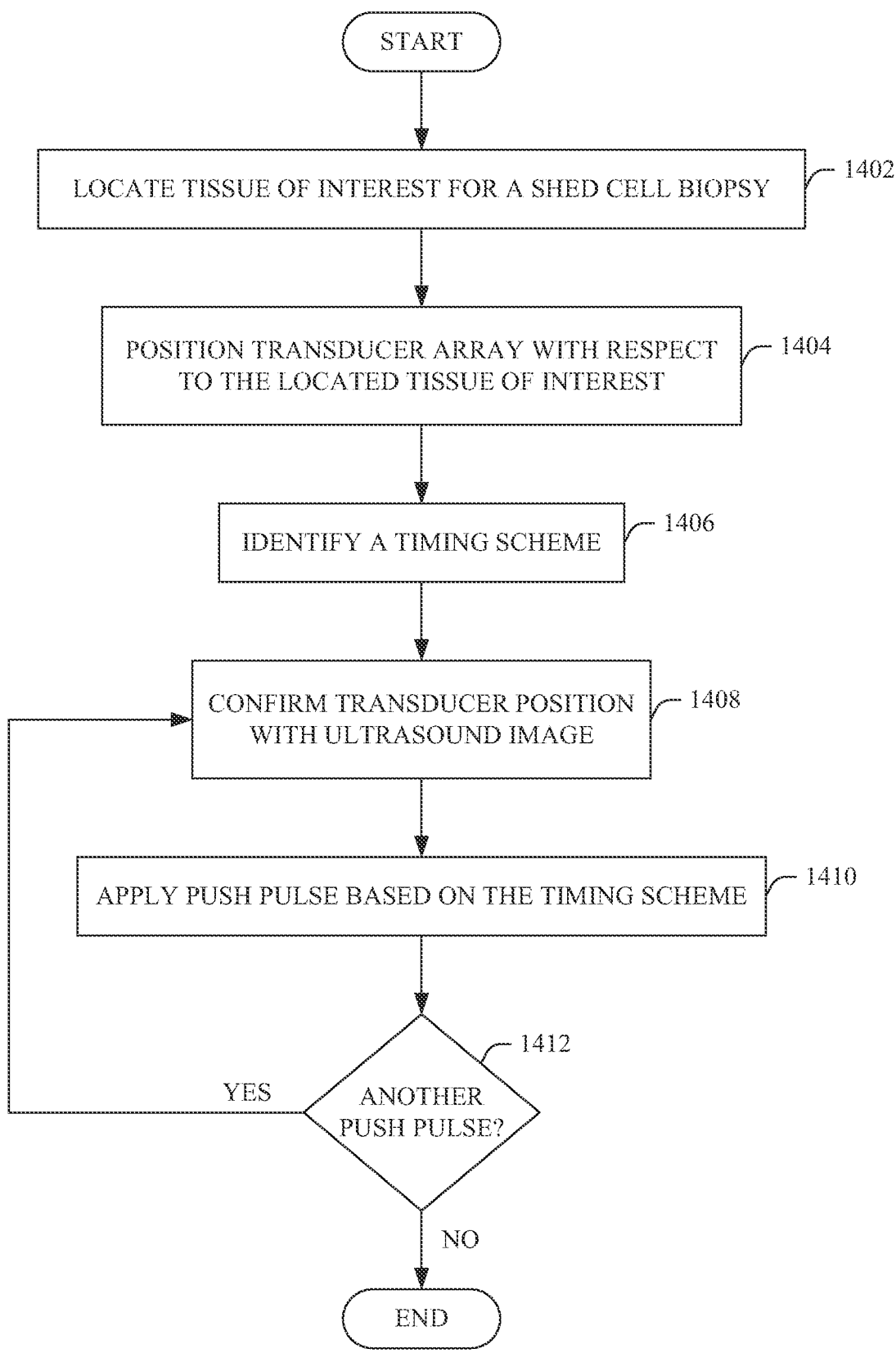
FIG. 14 illustrates another non-limiting example of a flow chart for a computer-implemented method, in accordance with an embodiment(s) herein.

FIG. 14 illustrates a non-limiting example of a flow chart for a computer-implemented method. It is to be appreciated that the ordering of the acts in the method is not limiting. As such, other orderings are contemplated herein. In addition, one or more acts may be omitted, and/or one or more additional acts may be included.

At 1402, tissue of interest for a shed cell biopsy is located, as discussed herein and/or otherwise. For example, an ultrasound image of anatomy is acquired. A region(s) of interest (ROI) is then placed over the image to bounds ductal tissue structure(s) of interest for targeting a push pressure pulse(s) based on anatomic information. The ROI can be created and placed via manually by a user, automated with an algorithm, or a combination thereof. At 1404, a transducer array is positioned with respect to the tissue of interest, as discussed herein and/or otherwise.

At 1406, a timing scheme of the timing schemes for the push pulse/imaging pulse mode is selected, as discussed herein and/or otherwise. As discussed herein, the system 102 may be configured with one or more modes of operation, including a push pulse mode, an imaging pulse mode and a push pulse/imaging pulse mode. In the push pulse mode only push pulses are generated, in the imaging pulse mode only imaging pulses are generated, an in the push pulse/imaging pulse mode both push pulses and imaging pulses are generated. The present example describes push pulse/imaging pulse mode.

FIG. 4 describes a non-limiting example of the timing sequence 402 of the timing sequences 314 for the push pulse/imaging pulse mode 312. The timing sequence 402 indicates transmit pressure amplitude versus time and includes the PRI 408, which includes the single pulse 410 with the pulse width 412 and the quiescence interval 414. Again, the PRI is in the range of 500 μs to 5 s, and, as such, the PRF is in the range of 2 kHz to 0.2 Hz. FIG. 2 describes the transmit pressure amplitude with the range of 50 kPa-5 MPa and the pulse 206 in the range of 20 μs-5 ms. FIG. 5 describes another timing sequence 502 for the push pulse/imaging pulse mode 312.

Table 1 shows a non-limiting example of transmit pulse characteristics for both a push pulse and an imaging pulse. From Table 1, the ultrasound frequency range for the push pulse is in a range of 1.0 to 10 MHz, the ultrasound frequency range for the imaging pulse is in a range of 1.0 to 20 MHz, and, for an abdominal procedure, an example ultrasound frequency for the push pulse and for the imaging pulse is 2.5 MHz. From Table 1, an example pulse width of the push pulse is 2000 cycles or 800 μs, and an example pulse width of the imaging pulse is 1-2 cycles or 0.5 μs. From Table 1, an example peak negative pressure amplitude at 2.5 MHz for the push pulse is less than 3.6 MPa, and an example peak negative pressure amplitude at 2.5 MHz for the imaging pulse is less than 3.6 MPa. From Table 1, an example MI for the push pulse is less than 1.9, and an example MI for the imaging pulse is less than 1.9.

At 1408 images can be generated and utilized to maintain and/or reposition the transducer array 108 with respect to the ductal tissue structure of interest. At 1410, a push pulse(s) is applied to the tissue of interest and images are generated based on the timing scheme. FIG. 8 shows the set of push pulses 802 applied to the ductal tissue structure of interest 704 bounded by the ROI 702 in the image 602. Again, the set of push pulses 802 may include a single pulse, multiple-simultaneous pulses and/or sequential pulses.

At 1412, it is determined if another push pulse is to be applied. This information may be part of the timing sequence, the protocol, user determined, etc. If it is determined that another push pulse will not be applied, the biopsy can then be performed. If it is determined that another push pulse will be applied, the steps 1408 and 1410 are repeated. At 1408, images can be generated with data acquired during the quiescence intervals 414, as described herein, and utilized to maintain and/or reposition the transducer array 108 with respect to the ductal tissue structure of interest. In another instance, images can be generated during a different interval(s). In another instance, images can be generated with a different imaging source. The steps 1408 and 1410 are repeated until it is determined that another push pulse will not be applied. The biopsy can then be performed.

As discussed herein, the human body is made up of cells that renew over time by shedding older cells and replacing them with newly made cells through normal physiologic processes, and, in some instances, the shed cells provide useful information and can be readily collected, e.g., for screening, etc., e.g., and as previously explained herein, ductal lining cells of the pancreas (and/or other shedding cells such as endothelial cells, etc.), due to their rapid turn-over rates, are well suited for screening for cancer, etc. and can be readily obtained via liquid biopsy sampling of fluids at a common ductal port of the pancreas.

The above method, in one instance, increases the number of shed cells at a given moment in time by an unforeseen amount, e.g., a couple orders of magnitude relative to the normal physiologic processes. In addition, the approach mitigates intravenous administration of a microbubble contrast agent and the shortcomings therewith. The method includes generating a push pulse (a narrow focused longitudinal wave with a pressure amplitude and width within in predetermined ranges), which, when applied to shedding tissue, provides local mechanical vibrations, including acoustic radiation pressure and shear wave propagation, which promote cell shedding.

The above method(s) can be implemented by way of computer readable instructions, encoded, or embedded on the computer readable storage medium, which, when executed by a computer processor, cause the processor to carry out the described acts or functions. Additionally, or alternatively, at least one of the computer readable instructions is carried out by a signal, carrier wave or other transitory medium, which is not computer readable storage medium.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include such additional elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a floppy disk drive, optical disk drive, and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "computer". The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the invention without departing from their scope. While the dimensions and types of materials described herein are intended to define the parameters of the various embodiments of the invention, the embodiments are by no means limiting and are exemplary embodiments. Many other embodiments will be apparent to those of skill in the art upon reviewing the above description.

This written description uses examples to disclose the various embodiments of the invention, including the best mode, and also to enable any person skilled in the art to practice the various embodiments of the invention, including making and using any devices or systems and performing any incorporated methods. The patentable scope of the various embodiments of the invention is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

Embodiments of the present disclosure shown in the drawings and described above are example embodiments only and are not intended to limit the scope of the appended claims, including any equivalents as included within the scope of the claims. Various modifications are possible and will be readily apparent to the skilled person in the art. It is intended that any combination of non-mutually exclusive features described herein are within the scope of the present disclosure. That is, features of the described embodiments can be combined with any appropriate aspect described above and optional features of any one aspect can be combined with any other appropriate aspect. Similarly, features set forth in dependent claims can be combined with non-mutually exclusive features of other dependent claims, particularly where the dependent claims depend on the same independent claim. Single claim dependencies may have been used as practice in some jurisdictions require them, but this should not be taken to mean that the features in the dependent claims are mutually exclusive.

What is claimed is:
1. An ultrasound system, comprising:
transmit circuitry configured to produce a push pulse electrical excitation signal; and
a transducer array configured to receive the push pulse electrical excitation signal and transmit a push pulse that produces acoustic longitudinal and shear wave propagation in tissue of interest, thereby promoting shedding of lining cells of the tissue of interest in connection with a biopsy of shed cells for the tissue of interest, wherein the push pulse is based on a pre-determined set of parameters stored in computer readable medium.

2. The ultrasound system of claim 1, wherein the acoustic longitudinal and shear wave propagations increase a number of the shed lining cells of the tissue of interest for the given time period.

3. The ultrasound system of claim 1, wherein the set of pre-determined parameters include a pulse width in a range of twenty microseconds to five milliseconds.

4. The ultrasound system of claim 1, wherein the set of pre-determined parameters include a pressure amplitude in a range of fifty kilopascals to five megapascals.

5. The ultrasound system of claim 1, wherein transducer array includes more than one transducer element, and the transmit circuitry is further configured to apply time delays to the more than one transducer element to focus the push pulse.

6. The ultrasound system of claim 1, wherein the acoustic longitudinal and shear wave propagations traverse in-plane of the transducer array.

7. The ultrasound system of claim 6, wherein the shear wave propagation traverses out-of-plane of the transducer array.

8. The ultrasound system of claim 1, further comprising:
receive circuitry configured to receive echo signals produced in response to an interaction of an imaging pressure wave and tissue; and
a beamformer configured to beamform the echo signals, producing an ultrasound image.

9. The ultrasound system of claim 8, wherein the transmit array is further configured to alternatively transmit the push pulse and the imaging pulse based on a predetermined timing sequence.

10. The ultrasound system of claim 1, wherein the push pulse promotes the shedding in an absence of microbubbles of a microbubble-based ultrasound contrast agent.

11. The ultrasound system of claim 1, wherein the set of pre-determined parameters include a combination of a pulse width value and a pressure amplitude value configured to provide a predetermined biologic effect.

12. The ultrasound system of claim 11, wherein the set of pre-determined parameters includes different combinations of pulse widths and pressure amplitudes for the predetermined biologic effect for different types of tissues.

13. The ultrasound system of claim 1, wherein the push pulse includes a single pulse.

14. The ultrasound system of claim 1, wherein the push pulse includes multiple-simultaneous pulses.

15. A computer-implemented method, comprising:
producing a push pulse electrical excitation signal; and
transmitting, based on the push pulse electrical excitation signal, a push pulse that produces acoustic longitudinal and shear wave propagation in tissue of interest, thereby promoting shedding of lining cells of the tissue of interest in connection with a biopsy of shed cells for the tissue of interest.

16. The computer-implemented method of claim 11, further comprising:
producing the push pulse electrical excitation signal based on a combination of a pulse width and a pulse pressure amplitude.

17. The computer-implemented method of claim 11, further comprising:
producing the push pulse electrical excitation signal based on a pre-determined timing sequence.

18. A computer readable medium encoded with computer executable instructions, which, when executed by a processor, cause the processor to:
produce a push pulse electrical excitation signal; and
transmit, based on the push pulse electrical excitation signal, a push pulse that produces acoustic longitudinal and shear wave propagation in tissue of interest, thereby promoting shedding of lining cells of the tissue of interest in connection with a biopsy of shed cells for the tissue of interest.

19. The computer readable medium of claim 18, wherein the push pulse has a frequency in a range of 1.0 to 10 MHz, a pulse width of 2000 cycles or 800 µs, and a peak negative pressure amplitude at 2.5 MHz of 3.0 MPa.

20. The computer readable medium of claim 18, where the computer executable instructions further cause the processor to:
increase the pulse width and decrease the pressure amplitude or increase the pressure amplitude and decrease the pulse width while maintaining a same biologic effect.

* * * * *